United States Patent [19]

Wakita et al.

[11] 4,402,951

[45] Sep. 6, 1983

[54] INSECTICIDAL COMPOSITION

[75] Inventors: Shizuo Wakita, Kawaguchi; Tokuko Umino, Kasukabe, both of Japan

[73] Assignee: Nippon Kayaku Kabushiki Kaisha, Tokyo, Japan

[21] Appl. No.: 252,839

[22] Filed: Apr. 10, 1981

[30] Foreign Application Priority Data

Apr. 25, 1980 [JP]  Japan .................................. 55-54228

[51] Int. Cl.$^3$ ..................... A01N 57/00; A01N 57/26; A01N 37/34
[52] U.S. Cl. ..................................... 424/200; 424/304
[58] Field of Search ................................ 424/200, 304

[56]  References Cited

U.S. PATENT DOCUMENTS

| 2,754,243 | 7/1956 | Gysin et al. | 424/200 |
| 3,894,149 | 7/1975 | Mast | 424/200 |
| 4,062,968 | 12/1977 | Fujimoto et al. | 424/304 |

OTHER PUBLICATIONS

Chemical Abstracts vol. 92: 41591m, (1980), Holan et al.

*Primary Examiner*—Douglas W. Robinson
*Attorney, Agent, or Firm*—Henry C. Nields

[57]  ABSTRACT

An insecticidal composition comprising as effective components 3-phenoxy-α-cyanobenzyl-1-(4-ethoxyphenyl)-2,2-dichlorocyclopropane carboxylate and O,O-diethyl-O-2-isopropyl-6-methylpyrimidin-4-yl phosphorothioate.

5 Claims, No Drawings

INSECTICIDAL COMPOSITION

DETAILED DESCRIPTION OF THE INVENTION

The present invention relates to an insecticidal composition comprising at least one adjuvant and an insecticidally effective amount of active ingredients which comprises 3-phenoxy-α-cyanobenzyl-1-(4-ethoxyphenyl)-2,2-dichlorocyclopropane carboxylate (hereinafter referred to as Compound A):

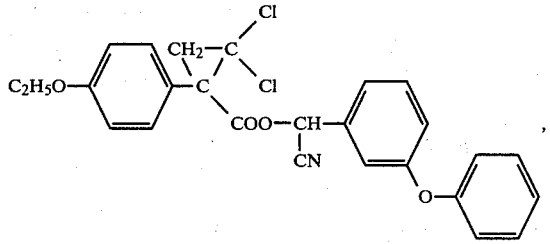

and O,O-diethyl-O-2-isopropyl-6-methylpyrimidin-4-yl phosphorothioate (hereinafter referred to as diazinon):

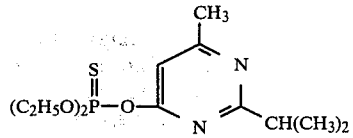

and a method for controlling insect pests.

In various fields of human life, there are numerous insect pests. For example, houseflies (*Musca domestica*) are typical insect pests to be exterminated. Houseflies produce several generations a year, act as a transmitter of infectious diseases, and cause discomfort when large in number. Occasionally, they cause reduction in number of hen's eggs and in the quantity of cow's milk. Green rice leafhoppers (*Nephotettix cincticeps*) are serious insect pests for rice. They increase in number by laying eggs to producing 5 to 6 generations a year. They destroy rice plants by spreading various virus diseases, and often degrade the quality of rice and reduce the yield thereof, since they suck the sap. The grass leaf rollers (*Cnaphalocrocis medinalis*) and rice plant skippers (*Parnara guttata*) produce 2 or 3 generations a year, and their larvae eat rice plant leaves over a long period of time to delay the growth of the rice plant.

Recently, as a result of repeated application of agricultural chemicals, there have appeared insect pests having resistance to the chemicals and it had become more difficult to control them.

And, in order to get a good control effect, it is necessary to increase the number of times of applications and the amount of chemicals. This has caused the problem on safety at the time of application and safety to humans and animals, and on agricultural economics.

Therefore, more effective insecticides are desired. The inventors have found that the insecticidal composition which comprises Compound A and diazinon controls the insect pests more widely and have more stable effect against insect pests having registance to organic phosphorous or carbamate insecticides compared with only Compound A or diazinon.

And the insecticidal composition of the present invention does not exhibit an additive effect owing to the characteristic properties of Compound A or diazinon but exhibit a synergistic effect.

Furthermore, the number of times of applications are reduced and the amount of the composition in the application is smaller than the sum of amounts of the active ingredients used when they are employed separately. Thus, safety at the time of application and safety to humans and animals are enhanced.

The composition comprising Compound A and diazinon of the present invention can be used directly or in combination with adjuvants in the form of an emulsion, wettable powder, powder, granules, aerosol, flowable suspension concentrates and U.L.V. preparation to be used in a very small amount by a method generally employed in the field of producing agricultural chemicals. At the time of the application, these formulations may be used either directly as they are or after dilution with water into a desired concentration and they are applied to insect pests or to a locus thereof.

As the adjuvants used in the present invention, there may be mentioned carriers (diluents), spreaders, emulsifiers, wetting agents, dispersants, fixing agents and disintegrators.

As the liquid carriers, there may be mentioned petroleum fractions such as kerosene and light oil, aromatic hydrocarbons such as toluene and xylene, methyl-naphthalene, cyclohexane, alcohols such as methanol, butanol and glycol, acetone, amides such as dimethyl-formamide, sulfoxides such as dimethylsulfoxide, animal oils, vegetable oils, fatty acids and fatty acid esters.

As the solid carriers, there may be mentioned clay, kaolin, talc, diatomaceous earth, silica, calcium carbonate, montmorillonite, bentonite, feldspar, quartz and alumina.

As the emulsifiers and dispersants, surfactants are used in general. The surfactants include anionic, cationic, nonionic and amphoteric surfactants such as sodium salts of higher alcohol sulfate, stearyltrimethyl ammonium chloride, polyoxyethylene alkylphenyl ether and laurylbetaine.

The content of the mixture of Compound A and diazinon in the insecticidal composition of the present invention is generally in the range of 0.5–95 wt.%, preferably 2–85 wt.%.

And preferable content can be given differently for respective types of formulations. For example, in the case of dust, the content of the mixture of Compound A and diazinon is 1.5–4.0%, that of adjuvants being 96.0–98.5%; in the case of granule and micro granule, the content of the mixture of Compound A and diazinon is 2.5–6.0%, that of adjuvants being 94.0–97.5%; in the case of wettable powder, the content of the mixture of Compound A and diazinon is 25–45%, that of adjuvants being 55–75.5%; in the case of aerosol the content of the mixture of Compound A and diazinon is 0.3–2.0%, that of the adjuvants being 98–99.7%; in the case of flowable suspension concentrates the content of the mixture of Compound A and diazinon is 20–40%, that of the adjuvants being 60–80%; in the case of U.L.V. preparations, the content of the mixture of Compound A and diazinon is 20–50%, that of adjuvants being 50–80%; in the case of emulsion the content of the mixtures of Compound A and diazinon is 30–50%, that of adjuvants being 50–70%.

The ratio of Compound A to diazinon is preferably in the range of 1:0.2–6.0 (parts by weight).

The amount of the composition of the present invention varies depending on the form thereof, the application method and other conditions. Generally, it is used in an amount of about 10–500 g, preferably 30–400 g (as active ingredients) per 10 are.

For example, the powders are used in an amount of 40–120 g (as active ingredients) per 10 are. The emulsions and wettable powders are used in an amount in the range of 40–250 g (as active ingredients) per 10 are. However, in special cases, the composition may be used in an amount below or above said range. Such a special amount is necessary in some cases.

These compositions may be used either alone or in the form of a mixture with a fungicide, herbicide, plant growth regulator, acaricide, agricultural and horticultural fungicide, soil sterilizer, soil conditioner and nematocide, as well as a fertilizer and another insecticide.

The present invention will be illustrated in detail with reference to the following preparation examples. However, varieties of the adjuvants and their mixing ratios are not limited to those shown below but they may be used in wide ranges. Parts are given by weight.

FORMULATION EXAMPLE 1

Emulsifiable concentrates

45 Parts of a liquid mixture of xylene and methylnaphthalene (1:1) was added to 20 parts of Compound A and 20 parts of diazinon to obtain a solution. Then, the solution was mixed with 15 parts of a mixture of an alkylphenolethylene oxide condensate and calcium alkylbenzenesulfonate (8:2) to obtain an emulsifiable concetrate.

The emulsifiable concentrates are to be diluted with water to a concentration of 1/1000–1/2000 and sprayed.

FORMULATION EXAMPLE 2

Wettable powders

10 Parts of Compound A and 30 parts of diazinon were mixed with 52.5 parts of synthetic silicon dioxide fine powder. The mixture was further mixed with 7.5 parts of another mixture comprising sodium laurate and sodium dinaphthylmethanesulfonate (1:1) and the whole was finely pulverized to obtain a powdery product. The resulting wettable powder is to be diluted with water to a concentration of 1/1000–1/2000 and sprayed.

PREPARATION EXAMPLE 3

Powders

95 Parts of a mixture of talc and calcium carbonate (1:1) was added to 1 part of Compound A and 2 parts of diazinon and the mixture was ground to obtain a sufficiently homogeneous dispersion. Further, 2 parts of synthetic silicon dioxide fine powder was added thereto to obtain a powder.

The powder is to be used as it is.

PREPARATION EXAMPLE 4

Aerosols

1 Part of Compound A and 4 parts of diazinon were dissolved in 45 parts of a mixture of methylnaphthalene and cyclohexane (1:1). The mixture was further mixed with 50 parts of freon to obtain a homogeneous solution, which was processed into an aerosol. The aerosol is to be used directly as a spray.

Typical examples showing the effects of the present invention will be given below. In the experiments, housefly, green rice leafhopper, grass leaf roller and rice plant skipper were used. However, the insect pests are not limited to these but the insecticidal compositions of the present invention can be used for controlling other insect pests such as german cockroach, house common mosquito (*Culex pipiens fallens*), house mosquito (*Culex pipiens molestas*), confused flour beetle, rice stem borer, rice leaf bettle, rice plant weevil, rice water weevil, diamond backmoth, tobacco cut worm (*Spodoptra litura*), cabbage armyworm (*Mamestra brassicae*), common cabbage worm, green peach aphid (*Myzus persicae*), cabbage aphid (*Breviocoryne brassicae*), green house whitefly (*Trialeurodes vaporariorum*), fall webworm (*Hyphantria cunea*), gypsy moth (*Lymantria dispar*), smaller tea torttirix and apple leaf miner (*Lithocolletis ringoniella*).

It will be apparent from the following experiments that, as compared with a case wherein the respective active ingredients are used separately, the composition of the present invention exhibits a higher direct insecticidal effect (first-acting property) and long-residual effect (persistency). The composition showed an excellent control effect in field tests as well.

EXPERIMENT 1

Test for control of housefly (*Musca domestica*)

1 μl of an acetone solution of an insecticidal composition diluted to a fixed concentration was applied to dorsal thorax of adult female of housefly (2–4 days after emergence) which is, resistant to organo phosphorous insecticides, by means of a micro applicator. 5 different concentrations were used. Each group comprised 25 adult female and the tests were carried out in two replications. 24 hours after the treatment, numbers of the surviving and dead houseflies were counted. The calculated death ratio was plotted on logarithmic probability paper to obtain a value of LD-50 (50% lethal dose).

The Co-toxicity coefficient was calculated according to the formula of Sun & Johnson [Jour. Econ. Ent. 53(5) 887–891 (1960)].

Co-toxicity coefficient of higher than 100 indicates the synergistic effect, a factor of around 100 indicates the additive action and the factor of less than 100 indicates the antagonistic effect.

The results are shown in Table 1.

TABLE 1

| Mixing ratio by weight Compound A Diazinon | Insecticidal effect LD-50 (μg/adult) | Co-toxicity coefficient of LD-50 |
|---|---|---|
| Only A:0 | 2.4 | — |
| 5:1 | 1.4 | 201 |
| 4:2 | 1.2 | 283 |
| 3:3 | 1.3 | 329 |
| 2:4 | 2.7 | 214 |
| 1:5 | 4.6 | 196 |
| 0:Only B | 20.0 | — |

EXPERIMENT 2

Tests for control of green rice leafhopper (*Nephotettix cincticeps*)

Seedlings of a rice plant (Saitama Mochi No. 10) were planted in 1/10,000 are pots. Each stump comprised 5 seedlings. When the seedlings grew to a height of 25 cm, they were treated with 1 kg/10 are of each dust by means of a bell jar duster. Immediately thereafter, a cylindrical wire netting having a diameter of 12 cm and a height of 30 cm was set and 15 female adult of green rice leafhoppers (collected in Kurume city, Fukuoka prefecture and reared in successive generations) were inoculated therein. The number of the green rice leafhoppers which had knocked down after a given period of time, and the rate of dead green rice leafhoppers after 24 hours were examined (first inoculation). Three days after the treatment, green rice leafhoppers were put therein in the same method as above and the rate of dead green rice leafhoppers was examined after 24 hours. (second inoculation) The tests were carried out in three replications.

The numbers of green rice leafhoppers which had knocked down after given periods of time were plotted on logarithmic probability paper to obtain values of KT-50 (50% knock down time). The results are shown in Table 2.

TABLE 2

| Concentration of mixture | | First inoculation | | Second inoculation |
|---|---|---|---|---|
| Compound A | + Diazinon | KT-50 (hr.) | Mortality (%) after 24 hrs. | Mortality (%) after 24 hrs. |
| 0.5 wt. % | + 0 wt % | 46.0 | 27 | 15 |
| 1.0 | + 0 | 9.1 | 70 | 30 |
| 0 | + 1.0 | 60.0 | 32 | 0 |
| 0 | + 2.0 | 24.0 | 50 | 0 |
| 0 | + 3.0 | 13.0 | 74 | 0 |
| 0.5 | + 1.0 | 5.7 | 97 | 45 |
| 0.5 | + 2.0 | 2.0 | 100 | 50 |
| 0.5 | + 3.0 | 1.8 | 100 | 60 |
| 1.0 | + 1.0 | 4.4 | 100 | 60 |
| 1.0 | + 2.0 | 1.5 | 100 | 72 |
| 1.0 | + 3.0 | 0.4 | 100 | 85 |

EXPERIMENT 3

Tests for control of green rice leafhopper (*Nephotettix cincticeps*)

1/10,000 are pots having a stump comprising 5 seedlings of a rice plant (Saitama Mochi No. 10) of 25 cm height were put on a turntable (16 r.p.m.). Each emulsifiable concentrate diluted with city water at given concentration was sprayed thereon at a distance of 1 m by means of a compressor spray gun (1 kg/cm$^3$). After drying with air, a cylindrical wire netting having a diameter of 12 cm and a height of 30 cm was set and 15 female adult of green rice leafhoppers (collected in Kumamoto city and reared in successive generations) were put therein. The number of the green rice leafhoppers which had knocked down after a given period of time, and the rate of dead green rice leafhoppers after 24 hours were observed. The tests were carried out in three replications. The numbers of green rice leafhoppers after given periods of time were plotted on a logarithmic probability paper to obtain values of KT-50.

Co-toxicity coefficients were calculated in the same manner as above. The results are shown in Table 3.

TABLE 3

| Mixture | | Insecticidal effects | | Co-toxicity coefficient of KT-50 |
|---|---|---|---|---|
| Compound A | + Diazinon | KT-50 (hr.) | Mortality (%) after 24 hrs. | |
| 50 ppm | + 0 ppm | 62.0 | 33 | — |

TABLE 3-continued

| Mixture | | Insecticidal effects | | Co-toxicity coefficient of KT-50 |
|---|---|---|---|---|
| Compound A | + Diazinon | KT-50 (hr.) | Mortality (%) after 24 hrs. | |
| 100 | + 0 | 12.0 | 73 | — |
| 0 | + 100 | 28.0 | 43 | — |
| 0 | + 200 | 13.0 | 57 | — |
| 0 | + 300 | 7.3 | 78 | — |
| 50 | + 100 | 8.0 | 90 | 431 |
| 50 | + 200 | 7.6 | 100 | 203 |

EXPERIMENT 4

Tests for control of the grass leaf roller (*Cnaphalocrocis medinalis*) and rice plant skipper (*Parnara guttata*) (field tests)

Field tests of grass leaf roller and rice plant skipper were carried out in a general paddy field of a farmer in Ageo city, Saitama prefecture. A paddy field under rice plant (Saitama Mochi No. 10) cultivation was divided in areas of 6 m × 10 m. 3 kg/10 are of each dust were sprayed thereon with a hand duster on July 30. The tests were carried out in two replications. 14 Days after the application, damage of the rice plant by grass leaf roller and rice plant skipper in 50 stumps in each area was examined. The results are shown in Table 4.

TABLE 4

| | | Rice plant skipper | | |
|---|---|---|---|---|
| Chemical | Conc. | Number of the alive skipper before the treatment | Number of the alive skipper after the treatment | Number of leaves damaged by grass leaf roller |
| Compound A | 1% | 21.0 | 14.5 | 25.0 |
| Compound A + diazinon | 1 + 2% | 15.0 | 1.0 | 10.0 |
| Diazinon | 2% | 16.0 | 13.5 | 29.5 |
| None | — | 10.0 | 50.5 | 40.5 |

What is claimed is:
1. An insecticidal composition comprising insecticidally effective amount of 3-phenoxy-α-cyanobenzyl-1-(4-ethoxyphenyl)-2,2-dichlorocyclopropane carboxylate and O,O-diethyl-O-2-isopropyl-6-methylpyrimidin-4-yl phosphorothioate in a weight ratio of 1:0.2–1:5.0 and an adjuvant therefor.
2. The insecticidal composition according to claim 1, wherein the content of the effective components in said composition is in the range of 0.5 to 95% on the weight basis.
3. The insecticidal composition according to claim 1, wherein the ratio by weight of 3-phenoxy-α-cyanobenzyl-1-(4-ethoxyphenyl)-2,2-dichlorocyclopropane carboxylate and O,O-diethyl-O-2-isopropyl-6-methylpyrimidin-4-yl phosphorothioate is in the range of 1.0:0.5–1.0:4.
4. A method for controlling insect pests which comprises applying to the insect pests or to a locus thereof an insecticidally effective amount of a mixture of 3-phenoxy-α-cyanobenzyl-1-(4-ethoxyphenyl)-2,2-dichlorocyclopropane carboxylate and O,O-diethyl-O-2-isopropyl-6-methylpyrimidin-4-yl phosphorothioate in a weight ratio of 1:0.2–1:5.0.
5. The method according to claim 4, wherein the ratio by weight of 3-phenoxy-α-cyanobenzyl-1-(4-ethoxyphenyl)-2,2-dichlorocyclopropane carboxylate to O,O-diethyl-O-2-isopropyl-6-methylpyrimidin-4-yl phosphorothioate is in the range of 1.0:0.5–1.0:4.0.

* * * * *

UNITED STATES PATENT AND TRADEMARK OFFICE
CERTIFICATE OF CORRECTION

PATENT NO. :   4,402,951
DATED      :   September 6, 1983
INVENTOR(S) :  Shizuo Wakita, et al.

It is certified that error appears in the above-identified patent and that said Letters Patent is hereby corrected as shown below:

On the Title Page, the following item [30] should be inserted between item [22] and item [51]:

--[30] Foreign Application Priority Data

April 25, 1980 [JP]   Japan .................................55-54228--

Signed and Sealed this

Sixth Day of August 1985

[SEAL]

*Attest:*

DONALD J. QUIGG

*Attesting Officer*    *Acting Commissioner of Patents and Trademarks*